July 8, 1958 F. W. ANDERSON Plant Pat. 1,723

NECTARINE TREE

Filed Oct. 29, 1957

WITNESS

Addison E. Avery

INVENTOR

Frederic W. Anderson

Webster & Webster

ATTYS.

United States Patent Office

Plant Pat. 1,723
Patented July 8, 1958

1,723

NECTARINE TREE

Frederic W. Anderson, Merced, Calif., assignor to Kim Bros., Reedley, Calif.

Application October 29, 1957, Serial No. 693,221

1 Claim. (Cl. 47—62)

This invention relates to a new and distinct variety of nectarine tree which bears exteriorly red, yellow fleshed, semi-freestone fruit characterized essentially by an extremely early ripening period. Such ripening period—being in advance of the harvest of any known commercial variety of nectarine—provides a nectarine for the market at least a week in advance of the present date of availability.

In comparison with the Early Sun Grand nectarine (United States Plant Patent No. 1,420), the fruit of the present variety—while generally similar in characteristics—ripens approximately ten days earlier, is not quite as large, and the flesh clings more to the stone.

As compared to the John Rivers nectarine (unpatented), the fruit of the present variety ripens a week to ten days earlier, has yellow instead of white flesh, is much firmer, and has considerably more red surface color.

The herein claimed variety of nectarine tree was originated by me, in the course of a long and continuing program seeking new and commercially acceptable varieties of nectarines, in my experimental nursery and orchard located near Merced, California.

Origination of the variety was accomplished as follows:

I undertook embryo culturing of a considerable number of the seeds which resulted from open pollination of the Early Sun Grand nectarine, and of the resultant seedlings a number—which, when in bearing and after careful observation, evidenced desirable characteristics, particularly early ripening—were selected for further trial by top-working on orchard trees; one of such selected and top-worked seedlings having been especially outstanding, and which is the present variety.

After such variety was originated, subsequent asexual reproductions—as by top-working—as performed by me in my nursery and orchard located near Merced, California, have come into maturity and are found to run true in all respects.

Figure 1:
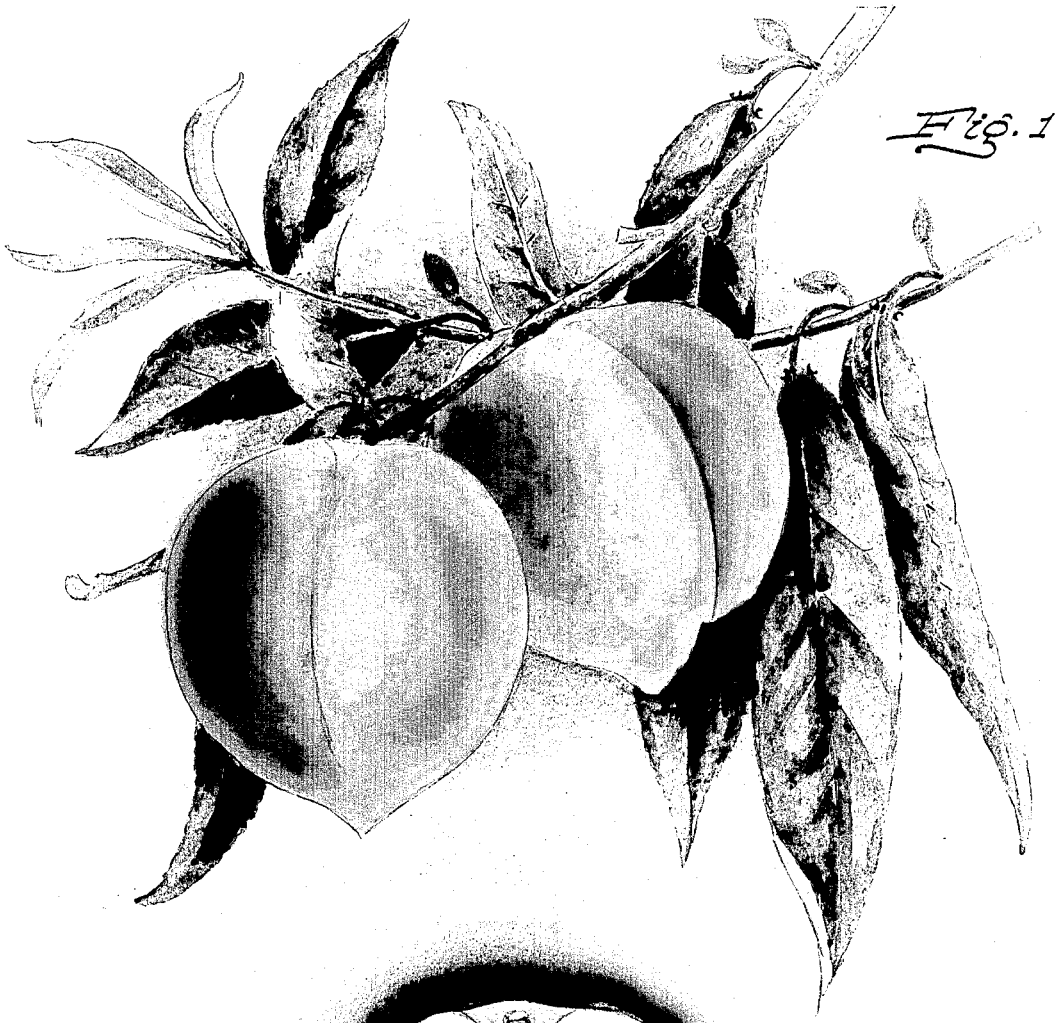
Fig. 1 is an elevation showing the fruit, together with twigs and leaves.
Figure 2:
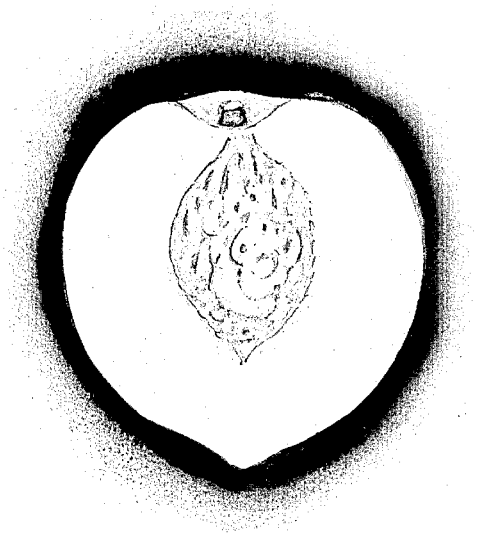
Fig. 2 is a sectional elevation of the fruit with the stone remaining in place.

Referring now more specifically to the pomological details of this new and distinct variety of nectarine tree, the following is an outline description thereof; all major color plate identifications being by reference to Maerz and Paul Dictionary of Color:

Tree:
- *Size.*—Large to medium.
- *Density.*—Dense to open.
- *Production.*—Productive.
- *Bearing.*—Regular bearer.

Trunk: Size—medium.

Branches: Size—medium.

Leaves:
- *Size.* — Medium. Average length — 5½" to 6". Average width—1¼" to 1½".
- *Form.*—Acuminate to lanceolate.
- *Thickness.*—Medium.
- *Margin.*—Crenate.
- *Petiole.*—Medium length; medium thickness.
- *Glands.* — Average number—four. Medium size; reniform. Position—usually two on petiole and two to three on blade.
- *Stipules.*—Drop early.
- *Color.*—Top side—medium green ((22–L–7 to 22–L–9), with a faint yellow cast. Under side—lighter green (22–L–5).

Flower buds:
- *Size.*—Medium.
- *Length.*—Medium.
- *Form.*—Conic.

Flowers:
- *Date of first and full bloom.*—Early to medium as compared with other varieties.
- *Size.*—Large—showy.
- *Color.*—Red anthers on stamens.

Fruit:
- *Maturity when described.*—Eating ripe.
- *Date of first picking.*—June 8, 1957.
- *Date of last picking.*—June 18, 1957.
- *Size.*—Medium. Average diameter axially—2½". Average transversely in suture plane—2⅜".
- *Form.*—Uniform; oblong.
- *Suture.*—Distinct; extends from base to beyond apex.
- *Ventral surface.*—Rounded; strongly lipped.
- *Cavity.*—Rounded; elongated in suture plane with suture showing on one side. Average depth—3/16". Average breadth—7/16".
- *Base.*—Rounded.
- *Apex.*—Short.
- *Pistil point.*—Apical.

Skin:
- *Thickness.*—Medium.
- *Texture.*—Medium.
- *Tendency to crack.*—None noted.
- *Down.*—Wanting.
- *Color.*—Relatively dark red (4–L–6 shading to 7–L–6), with orange-yellow ground color (11–J–11) showing through to a limited extent, and particularly about the apex.

Flesh:
- *Amygdalin.*—Scant.
- *Juice.*—Moderate.
- *Texture.*—Medium; melting.
- *Fibers.*—Few.
- *Ripens.*—Even.
- *Flavor.*—Sub-acid.
- *Aroma.*—Not pronounced.
- *Eating quality.*—Good.
- *Color.*—Yellow (9–J–5), shading to orange-yellow (9–J–8).

Stone:
- *Type.*—Semi-free.
- *Size.*—Medium. Average length—1⅜". Average breadth—⅞". Average thickness—¾".
- *Form.*—Ovoid.
- *Apex.*—Acute.
- *Kernels.*—Bitter.
- *Color.*—Beige (11–A–7), shading somewhat lighter (11–B–4) toward the bottom.

Use: Market; local.

Keeping quality: Good to medium.

Shipping quality: Good to medium.

The tree and its fruit herein described may vary in slight detail due to climatic and soil conditions under which the variety may be grown.

The following is claimed:

A new and distinct variety of nectarine tree, as illustrated and described, which bears exteriorly red, yellow fleshed, semi-freestone fruit characterized essentially by an extremely early ripening period; characterized further—in comparison with the Early Sun Grand nectarine—by ripening about ten days earlier, not quite as large of size, and flesh which clings more to the stone; and characterized additionally—in comparison with the John Rivers nectarine—by ripening about a week to ten days earlier, yellow instead of white flesh, firmer flesh, and more exterior red color.

No references cited.